(12) United States Patent
Klingenbeck-Regn et al.

(10) Patent No.: US 7,116,756 B2
(45) Date of Patent: Oct. 3, 2006

(54) X-RAY DIAGNOSTIC APPARATUS WITH A BODY MASS INDEX CALCULATOR FOR CONTROLLING X-RAY EMISSIONS

(75) Inventors: Klaus Klingenbeck-Regn, Nürnberg (DE); Michael Maschke, Lonnerstadt (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/896,653

(22) Filed: Jul. 22, 2004

(65) Prior Publication Data

US 2005/0031080 A1  Feb. 10, 2005

(30) Foreign Application Priority Data

Jul. 22, 2003  (DE)  ............... 103 33 295

(51) Int. Cl.
*H05G 1/10*   (2006.01)
(52) U.S. Cl. ...................................... 378/95
(58) Field of Classification Search ............... 378/62, 378/95, 195, 165, 209
See application file for complete search history.

(56) References Cited

U.S. PATENT DOCUMENTS 5,349,625 A * 9/1994 Born et al. .................... 378/95
6,585,328 B1 * 7/2003 Oexman et al. ............ 700/117

FOREIGN PATENT DOCUMENTS

DE  OS 198 09 738   9/1999
DE  OS 101 18 183   11/2002

* cited by examiner

*Primary Examiner*—Courtney Thomas
(74) *Attorney, Agent, or Firm*—Schiff Hardin LLP

(57) ABSTRACT

An x-ray diagnostic apparatus has an x-ray radiator, a control device connected thereto, a radiation detector and a patient-positioning table. The x-ray diagnostic apparatus has a device that calculates the BMI (body mass index) of the patient to be examined from detection of the body length and the weight. The device is connected with the control device to influence the parameters associated with obtaining an x-ray image.

12 Claims, 2 Drawing Sheets

X-RAY DIAGNOSTIC APPARATUS WITH A BODY MASS INDEX CALCULATOR FOR CONTROLLING X-RAY EMISSIONS

BACKGROUND OF THE INVENTION

1. Field of the Invention

The present invention concerns an x-ray diagnostic apparatus of the type having an x-ray radiator, a control device connected thereto, a radiation detector and a patient-positioning table.

2. Description of the Prior Art

In modern medical systems such as, for example, cardio systems, angiography systems or computed tomography systems, current patient data such as, for example, pulse, blood pressure etc. are only considered In part. An optimal adaptation of the generator settings for the respective applications to the patient thickness, however, is desired. Therefore, the system should be adaptable as flexibly as possible to the respective patient in order to achieve an optimally low radiation exposure of the patient.

From German OS 198 09 738, an x-ray diagnostic apparatus is known with a control unit to preset the radiation diaphragm setting necessary for the image acquisition, the control unit being provided with a computer that, based on direct access to patient data, makes a calculation for a presetting adapted to the patient, and adjusts the optimal diaphragm value by motors. An optimum adaptation of the generator settings to the patient thickness does not ensue in this known x-ray diagnostic apparatus.

Data such as the patient thickness can be taken from patient records, and thus can significantly deviate from the true current data. Often such data are not determined and used at all, but rather are only roughly estimated. Generally, a number of operating programs known as organ programs are available, with which the desired values for thin or thick patients are selected.

SUMMARY OF THE INVENTION

An object of the present invention is to provide an x-ray diagnostic apparatus of the type initially described, where an optimally comprehensive automated adjustment of suitable system data ensues.

The object is inventively achieved by an x-ray diagnostic apparatus having a device that calculates the BMI (body mass index) of the patient to be examined from the patient's body length and weight, the device being connected with the control device to influence parameters determining the x-ray radiation. The device also can be connected with an image system in order to patient-specifically adapt the organ programs stored in the system for controlling the voltage generator and image processing.

The patient-positioning table can embody a weighing device and/or sensors can be associated with the patient-positioning table that determine the body length of the patient to be examined. The sensors can thereby be integrated into the patient-positioning table.

The weighing device can be connected with a hospital information system (HIS) to which the automatically determined data are supplied for the electronic patient record (EPR).

The sensors can be photodiodes that determine the body size of the patient upon being covered by the patient. Alternatively, photoelectric barriers mounted laterally on the patient table as sensors can determine the body length. Temperature measurement sensors arranged as sensors in the patient table can be activated by the body temperature of the patient and thus determine the body length. The body length and/or the weight also can be inventively determined by pressure sensors or induction loops as sensors In the patient table.

The sensing device of the inventive x-ray diagnostic apparatus can be connected with a hospital information system that transmits the body length and the weight from an electronic patient record (for example according to the DICOM standard) to the device for the calculation of the BMI value for control of the voltage generator and/or image processing.

DESCRIPTION OF THE PREFERRED EMBODIMENTS

Figure 1:
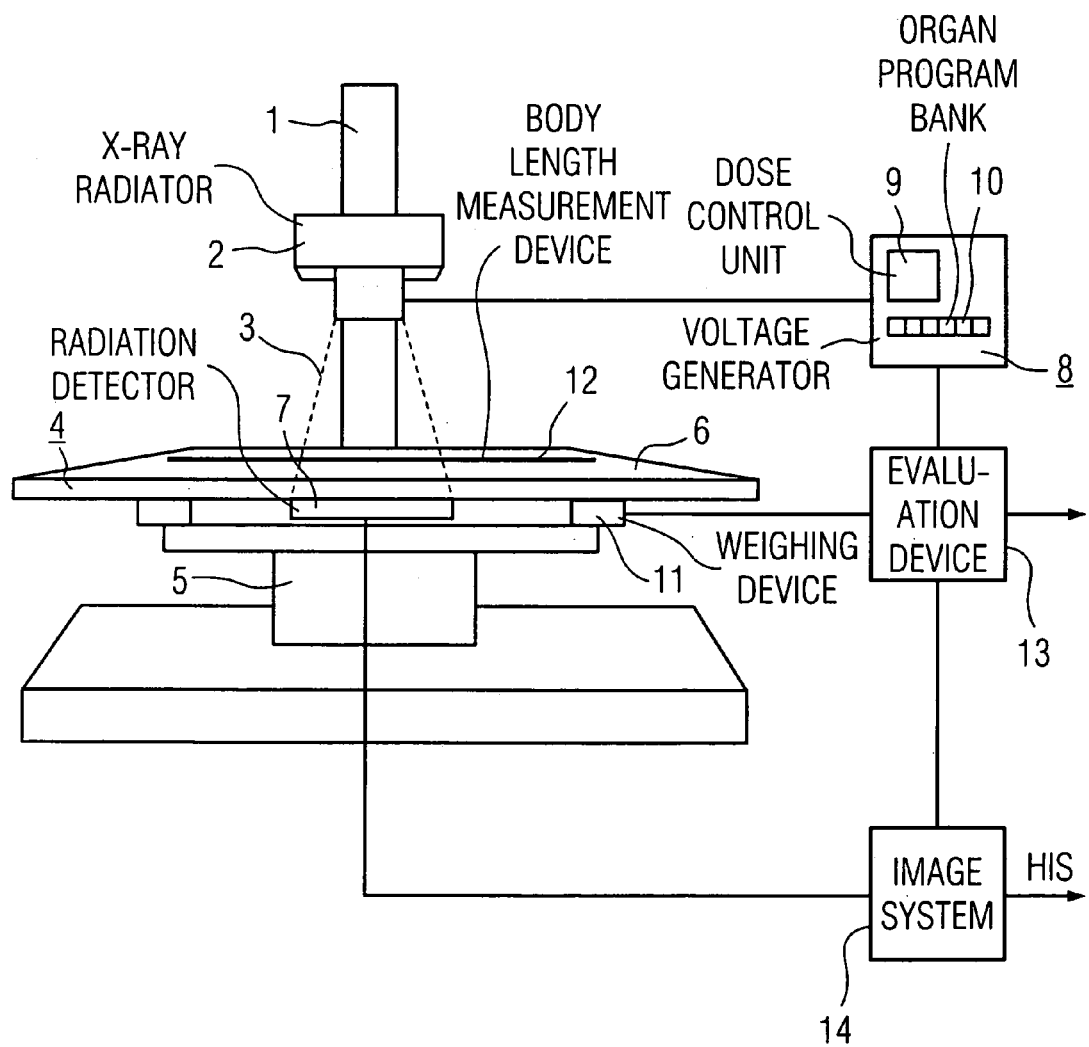
FIG. 1 illustrates an x-ray apparatus with an inventive device to determine weight and body length.

In FIG. 1, an x-ray diagnostic apparatus is shown that has an x-ray radiator mounted on a stand 1 as an x-ray source that generates an x-ray beam 3 directed downwardly, A displaceably mounted patient-positioning table 4 is attached to a base 5. A radiation detector 7 (for example a digital solid-state planar detector, an x-ray image intensifier television chain, or even an x-ray film cassette) is displaceably arranged under the positioning plate 6 of the patient-positioning table 4.

An x-ray generator 8 with a dose control unit 9 that can include an organ program bank 10 is connected with the x-ray radiator 2.

A weighing device 11 that, for example, can be realized by strain gauges (not shown) Is integrated into the patient-positioning table 4 of the x-ray diagnostic apparatus. Furthermore, the surface of the positioning plate 6 embodies sensors as a length measurement device 12 to determine the body size of the patient. The weighing device 11 and the length measurement device 12 are connected to an evaluation device 13 that calculates the body mass index (BMI) from these values. The BMI is calculated according to the equation $$BMI = \frac{G}{l^2},$$

wherein G is the weight in kilograms and I is the body length in meters. For example, a patient having a BMI of more than 25 is considered to be overweight.

The BMI calculated by the evaluation device 13 is transmitted to the dose control unit 9 in order to patient-specifically adapt the organ programs for the voltage generator and image processing stored in the system. For example, an overweight patient requires a higher radiation dose. Additionally, further data (such as the age of the patient) can be entered via the organ program bank 10.

The BMI calculated by the evaluation device 13 also can be transmitted to an image system 14 in order to patient-specifically adapt the parameters of the image processing.

The evaluation device 13 also can be connected with a hospital calculation system (HIS) to which the measured data is supplied for storage in the electronic patient record (EPR).

Figure 2:
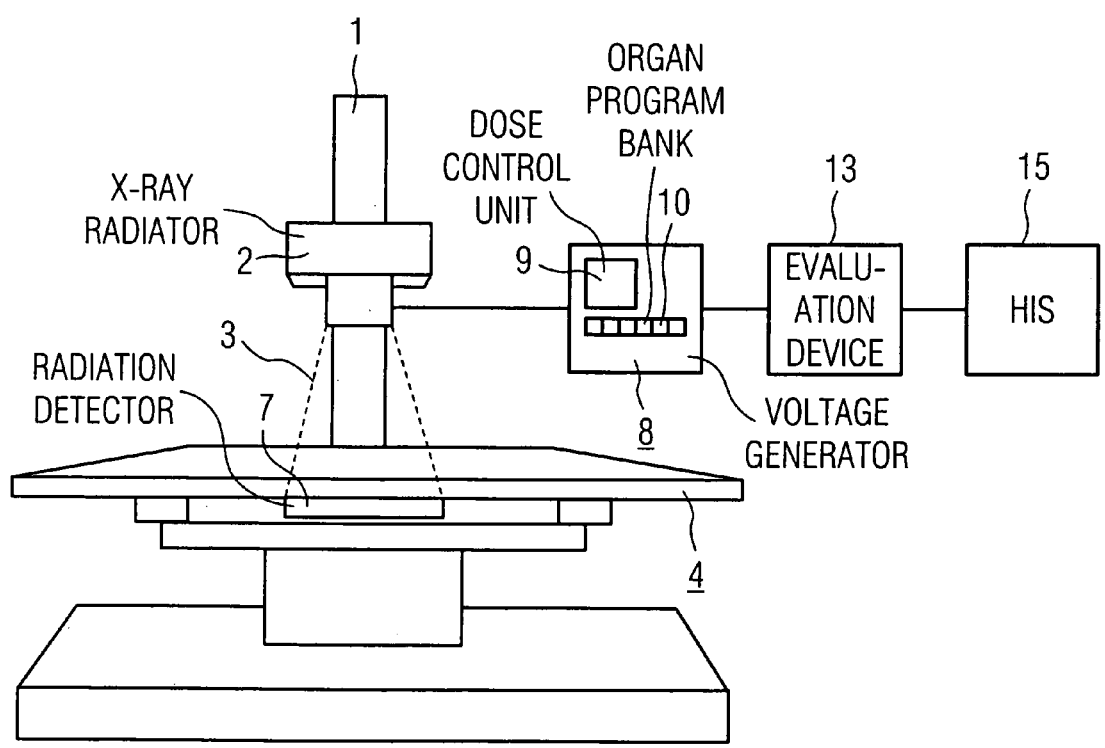
FIG. 2 illustrates a further embodiment of an inventive x-ray apparatus with the acceptance of data from the HIS.

A further embodiment of the inventive x-ray diagnostic apparatus is now shown in FIG. 2, In which a hospital information system (HIS 14) is connected to the evaluation device 13, from which hospital information system 14 the values already determined previously regarding weight and body size (that, for example, are stored in the electronic patient record (EPR)) are supplied to the evaluation device 13 to determine the BMI and therewith to influence the parameters of the organ program bank 10. The weighing device 11 and the length measurement device 12 thus are not needed.

Each x-ray diagnostic apparatus (such as, for example, a fluoroscopy system, an angiography system or a computed tomography system) is inventively provided with a weighing device 11, for example with strain gauges in the patient table. This weighing device 11 determines the body weight of the patient.

Additionally, each x-ray diagnostic apparatus has, for example, sensors arranged in the patient-positioning table 4 as a length measurement device 12 for determining the body length of the examined patient.

These sensors, for example, can be
photodiodes that determine the body size of the patient upon being covered by the patient,
temperature sensors which are activated by the body temperature of the patient and determine a size value,
pressure sensors, or
induction loops in the patient table that determine the body length.

The values determined for the patient weight and body size are to calculate the BMI, based on which parameters for the x-ray voltage generator 8 and/or image processing are patient-specifically corrected.

Given a missing measurement device in the system, the values from an electronic patient record (for example according to the DICOM standard) can inventively be used for the calculation of the BMI in order to determine body length and weight, and this value can be used to control the x-ray voltage generator and image processing.

The BMI can be calculated following the automatic detection of weight and body length. With this value, an automatic, patient-specific adaptation of the generator settings and image processing chain is possible. By the automatic, patient-specific adaptation, the x-ray radiation dose used can be reduced for the respective patient, and at the same time the image quality can be increased.

Furthermore, the surface of the positioning plate 6 embodies sensors for body fat analysis 12. The weighing device 14 is, as already specified, connected to the evaluation device 13 for correction of the generator data of the organ program bank 10.

Each x-ray system thus is inventively equipped with a weighing device 11 or 14 that, for example, can be integrated into the patient-positioning table 4. Additionally, the scale 11 can perform the body fat analysis. The sensors 11 to detect the values for this function can be integrated into the patient-positioning table 4.

With an automatic detection of weight and fat ratio of the patient at the beginning of a treatment, it is possible to optimally adapt the system parameters to the patient. From the weight and body fat ratio, the evaluation device 13 can determine the optimum parameters for the treatment and transfer them to the dose control unit 9 of the system. Further data, such as age, etc. can likewise be taken into account. A patent-specific organ program adaptation is possible that ensures a low dose exposure for the patient. At the same time, the image quality can be improved because the tissue property (meaning the ratio of fat to muscle tissue) can be taken into account In determining the absorption of the radiation. Furthermore, the automatically determined data as to weight and body fat ratio can be provided to the patient information system in the hospital for the electronic patient record.

Although modifications and changes may be suggested by those skilled in the art, it is the intention of the inventors to embody within the patent warranted hereon all changes and modifications as reasonably and properly come within the scope of their contribution to the art.

We claim as our invention:

1. An x-ray diagnostic apparatus comprising:
an x-ray radiator that emits x-rays;
a control device connected to said x-ray radiator for controlling the emission of x-rays from the x-ray radiator;
a patient-positioning table adapted to receive a patient thereon for irradiation by said x-rays;
a radiation detector on which said x-rays are incident after attenuation by a patient on the patient-positioning table; and
a body mass index calculator, supplied with data identifying a body length and a weight of a patient on the patient-positioning table, for calculating the body mass index of the patient on the patient-positioning table and for supplying said body mass index to said control device, said control device controlling the emission of said x-rays from said x-ray radiator dependent on said body mass index.

2. An x-ray diagnostic apparatus as claimed in claim 1 comprising an image processing system supplied with image data from said radiation detector for processing said image data, and wherein said body mass index calculator also supplies said body mass index to said image processing system, and wherein said image processing system uses said body mass index in processing said image data.

3. An x-ray diagnostic apparatus as claimed in claim 1 wherein said patient-positioning table comprises a weighing device for determining said weight, and for supplying said weight to said body mass index calculator.

4. An x-ray diagnostic apparatus as claimed in claim 1 comprising sensors associated with said patient-positioning table for determining said body length, and for supplying data representing said body length to said body mass index calculator.

5. An x-ray diagnostic apparatus as claimed in claim 4 wherein said sensors are built into said patient-positioning table.

6. An x-ray diagnostic apparatus as claimed in claim 5 wherein said sensors comprise photodiodes adapted to be covered by a patient on the patient-positioning table for determining said body length.

7. An x-ray diagnostic apparatus as claimed in claim 5 wherein said sensors comprises photosensitive barriers mounted laterally on said patient-positioning table for determining said body length.

8. An x-ray diagnostic apparatus as claimed in claim 5 wherein said sensors comprise temperature-measurement sensors in said patient-positioning table adapted to be covered by a patient on the patient-positioning table for determining said body length.

9. An x-ray diagnostic apparatus as claimed in claim 5 wherein said sensors comprise pressure sensors adapted to be covered by a patient on the patient-positioning table for determining said body length.

10. An x-ray diagnostic apparatus as claimed in claim 5 wherein said sensors comprise induction loops in said patient-positioning table adapted to be covered by a patient on the patient-positioning table for determining said body length.

11. An x-ray diagnostic apparatus as claimed in claim 1 comprising a pressure sensor in said patient-positioning table adapted to interact with a patient on the patient-positioning table for determining said weight, and for supplying said weight to said body mass index calculator.

12. An x-ray diagnostic apparatus as claimed in claim 1 wherein said body mass index calculator comprises a communication interface to a hospital information system for automatically supplying data representing the body mass index, the body length and the weight of a patient on the patient-positioning table for inclusion in an electronic patient record of a patient on the patient-positioning table.

* * * * *